United States Patent
Woo

(10) Patent No.: US 7,444,882 B2
(45) Date of Patent: Nov. 4, 2008

(54) MATERIAL FAILURE PREDICTION/STRESS/STRAIN DETECTION METHOD AND SYSTEM USING DEFORMATION LUMINESCENCE

(76) Inventor: Geoffrey Woo, 32055 Pacifica Dr., Rancho Palos Verdes, CA (US) 90275

( * ) Notice: Subject to any disclaimer, the term of this patent is extended or adjusted under 35 U.S.C. 154(b) by 164 days.

(21) Appl. No.: 11/294,554

(22) Filed: Dec. 6, 2005

(65) Prior Publication Data

US 2008/0236294 A1    Oct. 2, 2008

(51) Int. Cl.
*G01L 1/24*  (2006.01)
*G01B 11/16* (2006.01)

(52) U.S. Cl. .......................... 73/800; 356/32
(58) Field of Classification Search ............ 73/800, 73/760, 788; 356/32–35.5
See application file for complete search history.

(56) References Cited

U.S. PATENT DOCUMENTS

| | | | | |
|---|---|---|---|---|
| 3,631,713 A | * | 1/1972 | Marom et al. .................. | 73/577 |
| 4,667,095 A | * | 5/1987 | Hatanaka et al. ............. | 250/226 |
| 4,680,470 A | * | 7/1987 | Heald ...................... | 250/358.1 |
| 6,628,375 B2 | * | 9/2003 | Xu et al. ..................... | 356/32 |
| 6,710,328 B1 | | 3/2004 | Mastro et al. | |

OTHER PUBLICATIONS

Chandra, B.P. "Acoustic and Photon Emission During Mechanical Deformation of Coloured Alkali Halide Crystals." J. Phys. D: Appli. Phys. 17 (1984): 117-123.*

Xu, C., Liu, Y.., Akiyama, M., Nonaka, K., Zheng, X. "Visualization of Stress Distribution in Solid by Mechanoluminescence." Proc. SPIE vol. 448, (2001): 398-407.☐☐.*

Oldyrev P. P., Upitis Z. T., Krauya U. É. "Application of Mechanoluminescence for Examining Failure of Fiberglass Plastics in Axial Static and High-Cycle Loading." Mechanics of Composite Materials vol. 20, No. 7 (1985): 771-777.☐☐.*

Krauya U. É., Kalnin, P. P., Yansons, Ya. L., Strukovskis, A. A., "Investigation of Failure of Composite Materials by the Method of Deformation Luminescence in a Broad Velocity Range of Loading." Strength of Materials vol. 23, No. 9 (1991): 992-996.*

Xu, C., Yamada, H., Wang, X., "Development of Strong Elasticoluminescence from Ferroelectric Phase" 2004 IEEE Ultrasonics Symposium 914-917.*

Zimmerman K.A., Langford S.C., Dickson J.T. and Dion R.P. "Electron and Photon Emission Accompanying Deformation and Fracture of Polycarbonate" Journal of Polymer Science: Part B: Polymer Physics, vol. 31, 1229-1243 (1993).*

"Fracture." Academic Press Dictionary of Science and Technology. 1992. CredoReference. Accessed on Dec. 12, 2007 <http://www.credoreference.com/entry/3106790>.*

* cited by examiner

*Primary Examiner*—Edward Lefkowitz
*Assistant Examiner*—Punam Patel
(74) *Attorney, Agent, or Firm*—Stites & Harbison PLLC; Ross F. Hunt, Jr.

(57) ABSTRACT

A method and apparatus are provided for detecting strain, stress, fatigue and incipient failure in materials. A detector (e.g., a photomultiplier tube) is used to detect photonic emissions from a material under test. Data based on the detected photonic emissions is displayed in real time so as to enable real time analysis of the data in determining strain, stress, fatigue and/or incipient failure.

4 Claims, 1 Drawing Sheet

MATERIAL FAILURE PREDICTION/STRESS/STRAIN DETECTION METHOD AND SYSTEM USING DEFORMATION LUMINESCENCE

FIELD OF THE INVENTION

The present invention relates to an improved method and system for predicting material failure as well as for detecting stress and strain in materials.

BACKGROUND OF THE INVENTION

For years, the fields of aerospace and structural engineering have been hindered by the inability of scientists to accurately detect structural stress, to analyze the degrading effects of long-term fatigue, and, most importantly, to predict when a structure or structural member will break or fail.

Particularly in the cases of advanced composites for military aircraft and aluminum engines for high performance automobiles, systematic fatigue is nearly impossible to detect (see Case, S W., and K L. Reifsnider. *Fatigue of Composite Materials*. Virginia Polytechnic Institute and State University. 20 Dec. 2004. In this regard, there are usually no signs of material fatigue until the structure actually begins to break down or crumble.

Current commercial stress detection systems typically involve the use of interferometers or diffractometers, which essentially measure how much a material is compressed (see Pirling, T, and R Wimpory. *Stress measurements on D1A: a new high precision strain-scanner*. Institut Laue-Langevin. 17 Dec. 2004.). This technique is, in general, ineffective because all materials have a normal elastic range, and it is difficult to immediately distinguish the change from the elastic region to the plastic region (see *Hookes Law—Strength (Mechanics) of Materials*. Engineers Edge. 17 Dec. 2004.). Further, this method does not determine internal damage nor does it show stress levels within the interior of the material.

As designers and engineers push their creations to their design limits, the increasing stress demands for engines, aircraft, and skyscrapers spawn problems such that a single deformed bolt could lead to failure and disaster. The inability to detect material stress can effectively mean the difference between life and death.

Substantial resources have been spent on costly reconstructions and improvements. Engineers have been trying to battle the problem of material fatigue by adding reinforcements upon reinforcements to their structures, while chemists attempt to formulate new alloys and composites in hopes of finding the next ultra-light, ultra-strong alloy (see Britt, Robert R. *Space Age Metal: New Titanium Alloys Near 'Magic' Strength Threshold*. 22 Apr. 2003. Space.com. 17 Dec. 2004. <http://www.space.com/businesstechnology/technology/new_alloy_030422.html>). However, even the most advanced materials weaken and it is inevitable that repairs and replacements are needed. Thus, while developing new materials is important, accurate detection and quick replacement of damaged components are key to solving the problem of material fatigue.

As discussed below, the present invention, in accordance with one aspect thereof, concerns the phenomena of deformation luminescence and its application as an indicator of material fatigue and predictor of failure. Deformation luminescence is the emission of light produced when a regular lattice structure, such as a crystal, is plastically deformed. It appears from the literature that the effect of deformation luminescence was first discovered in the late 1950's (see Butler, C T. "Room-Temperature Deformation Luminescence in Alkali Halides." *Physical Review* 141.2 (1966): 750-757). This phenomenon is not to be confused with triboluminescence, which is the emission of light from electrical sparks produced when a material is fractured or scratched (typically piezoelectric) (see Hagihara, T. "Deformation Luminescence in Gamma-Irradiated Alkali Halides." *Physics Letters A* 137. (1989): 213-216).

Several studies have been conducted attempting to explain deformation luminescence (see Molotskii, M I., and S Z. Shmurak. "Elementary Acts of Deformation." *Physics Letters A* 166. (1992): 286-291). The most comprehensive theory to date proposes a dislocation mechanism for deformation luminescence. According to this theory, ionizing radiation, as well as other high energy processes, dislocate electrons and ions in the regular lattice structure. Electrons are relocated into high energy electron wells known as F-centers, which color the crystal. When the crystal is plastically deformed, the stress overcomes the F-centers and subsequently ionizes them. The electrons are then released in the conduction band and dropped into a lower level well. If an electron recombines with a luminescence center, deformation luminescence is observed (see Hayashiuchi, Y. "Theory of Deformation Luminescence in KCI Crystal." *Physics Letters A* 147. (1990): 245-249). According to some studies, ionizing radiation greatly amplifies photon emissions by increasing the number of F-centers within the lattice structure (see Srinivasan, M., and DeWerd, L A. "The Effect of Plastic Deformation on the Thermoluminescence of LiF (TLD-100) single crystals." *Journal of Physics D: Applied Physics* 6. (1973): 2142-2149). The concentration of F centers is postulated to be exactly proportional to the intensity of deformation luminescence.

SUMMARY OF THE INVENTION

In accordance the invention, a method is provided for, inter alia, predicting material failure and for providing an improved indication of material fatigue by correlating photon emissions to stress and strain. Broadly speaking, by analyzing the emissions (preferably, photonic emissions and, more preferably, deformation luminescence) from a material under test, the overall health of the material can be assessed In accordance with one aspect of the invention, there is provided a method for predicting failure of a material, said method comprising the steps of:

detecting photonic emissions from a material under test and counting the number of photons emitted by the material over time; and comparing the number of photons counted with a predetermined constant value based on the cumulative total of photons at failure for a comparable material so as to predict incipient failure of the material under test.

Preferably, the detecting step comprises measuring the intensity of deformation luminescence produced by the material.

Advantageously, a photomultiplier tube is used in the detecting step.

According to another aspect of the invention there is provided a method for detecting stress or strain in a material, said method comprising the steps of:

measuring the intensity of deformation luminescence produced by the material by detecting photonic emissions from the material; and using the detected photonic emissions to determine stress or strain in the material.

Preferably, the method is used to predict failure in addition to detecting stress or strain.

In one embodiment, the detecting step comprises counting the number of photons emitted over time by the material.

Preferably, a photomultiplier tube is used in the detecting step.

Preferably, the step of determining stress or strain comprises collecting in real time data relating to the photonic emissions so as to enable real time analysis of the data.

In accordance with a further aspect of the invention, there is provided a method for detecting a crack in a material, said method comprising the steps of:

detecting photonic emission from the material; and comparing the photonic emissions detected with a predetermined reference level of photonic emissions for an uncracked material.

In a preferred implementation, the detected photonic emissions are monitored for a spike therein indicative of the presence of a crack or small fracture in the material.

According to another aspect of the invention, there is provided a method for detecting fatigue in a material, said method comprising the steps of:

detecting photonic emissions from the material; and using the detected photonic emissions to determine fatigue in the material.

Preferably, the detecting step comprises measuring the intensity of deformation luminescence produced by the material.

The detecting step preferably comprises counting the number of photons emitted.

Preferably, in the determination of fatigue, a determination is made as to when the number of photons counted by the counting step approaches a predetermined constant value calculated based on a cumulative total for photon emissions up to fracture.

In another preferred implementation, the photonic emissions are analyzed for a sudden increase therein indicative of hysteresis.

According to yet another aspect of the invention, there is provided an apparatus for detecting strain, stress, fatigue and incipient failure in materials, said apparatus comprising:

a detector for measuring the intensity of deformation luminescence produced by a material under test by detecting photonic emissions from the material under test; and means for deriving data from the detected photonic emissions for display in real time so as to enable real time analysis of the data in determining at least one of strain, stress, fatigue and incipient failure.

Preferably, the detector comprises a photon counter for counting the number of photons emitted by the material under test.

Advantageously, the photon counter comprises a photomultiplier tube.

Preferably, the apparatus further comprises means for comparing the number of photons emitted over time counted by said photon counter with a predetermined constant value based on the cumulative total of photons at failure for a comparable material so as to provide a prediction of incipient failure of the material under test.

Further features and advantages of the present invention will be set forth in, or apparent from, the detailed description of preferred embodiments thereof which follows.

DESCRIPTION OF THE PREFERRED EMBODIMENTS

Figure 1:
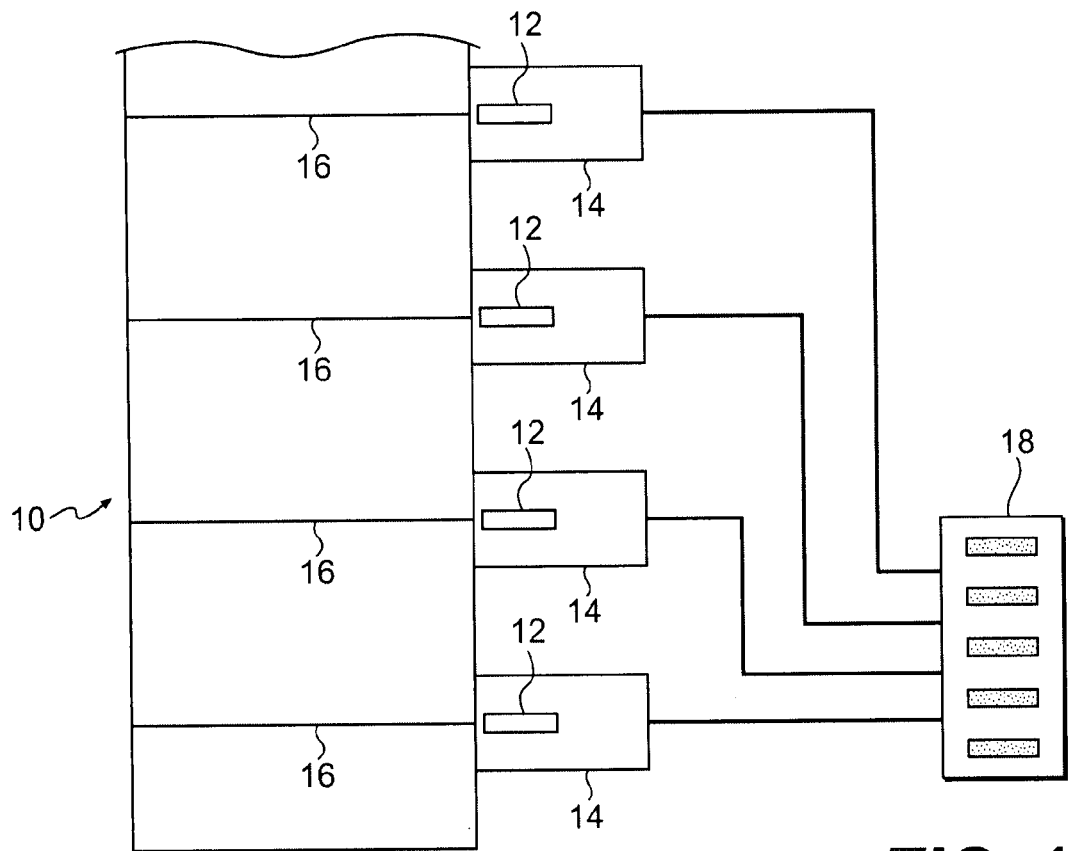
FIG. 1 is a highly schematic block diagram representation of a deformation luminescence detection system in accordance with one embodiment of the invention.

Referring to FIG. 1, there is shown a highly schematic representation of a structure 10 that is being monitored. As illustrated, a series of sensors 12, which, in one preferred embodiment, comprise conventional photomultiplier tubes (PMTs), are placed at vital areas of the structure 10, i.e., at areas, indicated at 16, where stress is most likely. It will be appreciated that while the following description makes reference to photomultiplier tubes (PMTs) other photon detectors/counters can also be used. The sensors (PMTs) 12 are housed in lightproof housings 14 so that outside light does not interfere with the measurements made by the sensors (PMTs) 12.

The outputs of each of the sensors (PMTs) 12 are connected to, or the output data from each is otherwise communicated to, a control center 18 at which technicians and/or computer programs analyze the output data to detect material fatigue and/or predict material failure. This analysis is discussed in more detail below.

Figure 2:
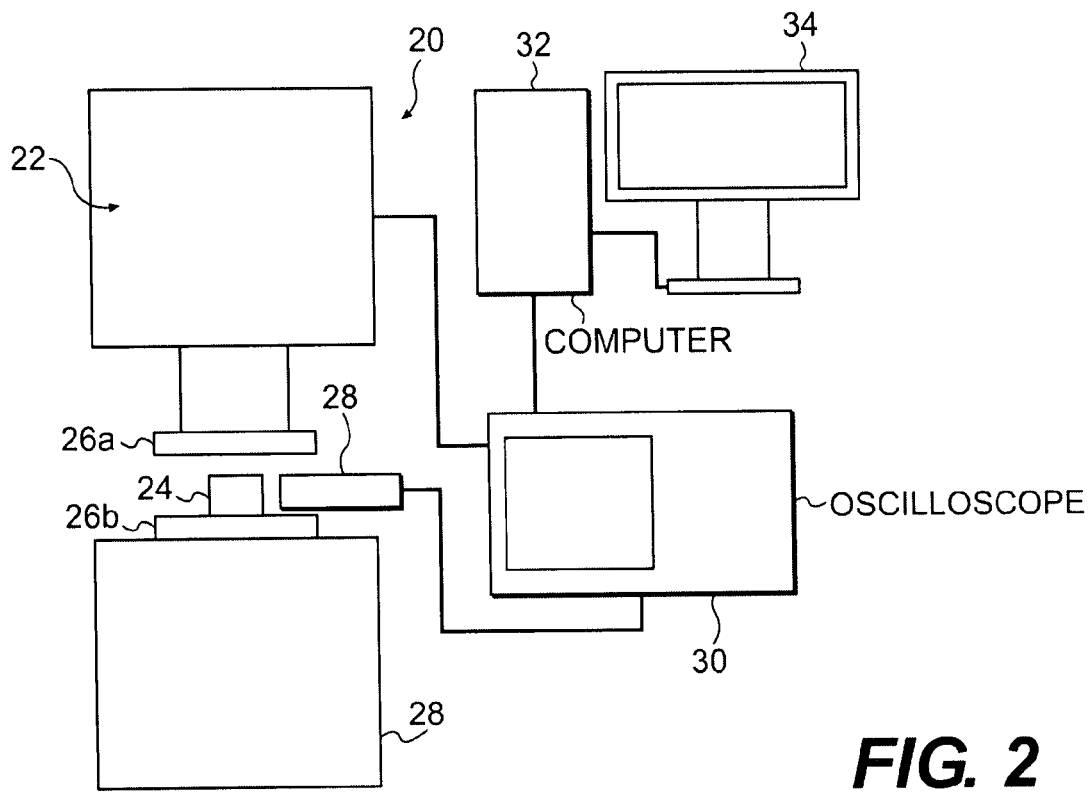
FIG. 2 is a schematic diagram of a test setup used in carrying out testing employing an apparatus embodiment of the invention.

Referring to FIG. 2, an experimental setup or apparatus 20 is shown which is used in explaining some of the principles of the invention in connection with deriving and analyzing stress and strain data. In the experimental apparatus 20, a conventional material testing or compression unit 22, viz., an Instron 4483, was used to compress a sample 24. The compression was carried out by using a pair of flat plates 26a and 26b, plate 26a being movable, and plate 26b being mounted on a base member 28 and being adapted to support the sample 24 thereon. Compression unit 22 includes a load cell (not shown) which in the exemplary non-limiting embodiment under consideration, comprises a 30,000 lb, 15,000 Kg., 150 KN load cell, and which provides stress and strain data to an oscilloscope 30.

A photomultiplier tube (PMT) 32 is used to sense the deformation luminescence (DL) produced by sample 24 in response to compression thereof. In the exemplary, non-limiting example, PMT 32 may be a R2027, 1250V, 0.1 mA photomultiplier tube.

As shown, oscilloscope 30 may be connected to a computer 32 with an associated monitor 34.

In the specific example under consideration, specimen or sample 24 comprises a Lithium Fluoride (LiF) crystal, and nominally pure LiF crystals were procured from Hilger Crystals through Spectra Physics.

The data was recorded in volts on the oscilloscope 30. Conversion factors for load and photon emissions are as follows:

5V Load=15 klb

1V Photon Emission=$1.75 \times 10^{10}$ photons/sec

The photon emission conversion factor was calculated using photomultiplier datasheets for photomultiplier tube 28 for quantum efficiency, etc. and taking into consideration the limited window of the tube 28.

For alkali halides, namely Lithium Fluoride (LiF), it was necessary to correct the recorded intensities for absorption by F-centers through the relation:

$$I_a = I_r \left[ \frac{1 - e^{-ad}}{ad} \right]$$

where a ($0.74 \times 10^{-3}$ cm$^{-1}$ for pure LiF) is the absorption coefficient (affected by radiation dosage), in 1/cm at the recorded wavelength, d is the thickness of the crystal in cm, Ia is the intensity observed without absorption and Ir is the intensity actually recorded.

For the purpose of light-proofing, triple layers of light absorbent fabric and paper (not shown) were cloaked entirely around the experiment area. The photomultiplier 28 was powered to 700 volts to detect any significant light leakage.

The two flat steel anvils or plates 26a and 26b were attached to the grip provided by compression unit 22. A steel block (not shown) was inserted between the anvils 26a, 26b to provide room for the photomultiplier 28, which was attached to a stand (not shown) positioned adjacent to the grips of unit 22 at a spacing 1 centimeter away from the crystal sample 24.

The oscilloscope 30 was programmed to take data at 250 Sa/s. The load signal was from the load cell (not shown) of unit 22 inputted at 100 mV/div, and the photomultiplier signal from PMT 28 at 5 mV/div. Load in mV was converted into pounds per square inch (psi), strain was measured by the extension method and converted into percentage, and the DL in mV was converted into photons/sec.

The samples 24, which were of two groups, respectively of dimensions 5×5×5 mm and 10 mm×10 mm×10 mm, could be positioned reproducibly at the same spot by method of guide and push, so the crystal 24 could face perpendicular to the photomultiplier 28.

The LiF crystals 24 of one group were irradiated with a 2700 curie Co-60 source. The crystals were wrapped in aluminum foil, coded, and irradiated for 12 hours at a distance of 20 cm for a total dose of 800 kiloRoentgens. The source temperature was kept at 20° C. The samples were left in their aluminum coating for 72 hours to allow the afterglow to decay to levels well below the DL range.

To provide a non-irradiated sample control, a 10 mm cube of non-irradiated LiF was also inserted into the unit 22. The anvils 26a, 26b were started together at 0.002 inches/min. Load vs. photon emission data were recorded by the oscilloscope 30 and stress vs. strain data was taken directly from the load cell of the unit 22.

To provide a compression control, 5 mm and 10 mm cubes of irradiated LiF were inserted into the unit 22. The anvils 26a, 26b were started together at 0.002 inches/min for the 5 mm cube and 0.04 inches/min for the 10 mm cube. Load vs. photon emission data were recorded by the oscilloscope 30 and stress vs. strain data was taken directly from the unit 22.

To provide an artificial (manipulated) surface fracture, a 10 mm cube of irradiated LiF was cut with a razor. A 1.5 mm incision was made. Afterward, the corresponding sample 24 was inserted into the unit 22. The anvils 26a, 26b were started together at 0.002 inches/min and cycled to 300 pounds per square inch and then to 500 pounds per square inch, over 5 trials. Load vs. photon emission data were recorded by the oscilloscope 30 and stress vs. strain data was taken directly from the unit 22.

To provide varied (manipulated) load speeds, irradiated LiF cubes 24 were inserted into the unit 22. The speeds used in this particular example were 0.002, 0.016 and 0.032 inches/min. Load vs. photon emission data were recorded by the oscilloscope 30 and stress vs. strain data was taken directly from the unit 22.

In addition, in order to provide (manipulated) cycling over a range of 10-200 psi (i.e., within the linear/elastic region), a 5 mm cube sample 24 of irradiated LiF was inserted into the unit 22, and the anvils 26a, 26b were started together at 0.002 inches/min between 0 and 200 pounds per square inch. This cycling occurred for 5 trials. Load vs. photon emission data were recorded by the oscilloscope 30 and stress vs. strain data was taken directly from the unit 22.

Cycling was also carried out over a range of 0-300 psi (i.e., reaching the end of the linear/elastic region). A 5 mm cube sample 24 of irradiated LiF was inserted into the unit 22 and the anvils 26a, 26b were started together at 0.002-inches/min between 0 and 300 pounds per square inch. This cycling occurred for 5 trials. As before, load vs. photon emission data were recorded by the oscilloscope and stress vs. strain data was taken directly from the unit 22.

In addition, cycling was carried out over a range of 0-400 psi (reaching the end of the linear/elastic region). A 5 mm cube sample 24 of irradiated LiF was inserted into the unit 24 and the anvils 261, 26b were started together at 0.002 inches/min between 0 and 400 pounds per square inch. This cycling occurred for 5 trials. Again, load vs. photon emission data were recorded by the oscilloscope 30 and stress vs. strain data was taken directly from the unit 22.

Further, cycling was also carried out over a range of 0-500 psi (reaching the end of the linear/elastic region). A 5 mm cube sample 24 of irradiated LiF was inserted into the unit 22 and the anvils 26a, 26b were started together at 0.002 inches/min between 0 and 500 pounds per square inch. This cycling occurred for 5 trials. As above, load vs. photon emission data were recorded by the oscilloscope 30 and stress vs. strain data was taken directly from the init 22.

In addition, cycling was carried out over the range of 0-600 psi (past the linear/elastic region). A 5 mm cube sample 24 of irradiated LiF was inserted into the unit 22 and the anvils 26a, 26b were started together at 0.002 inches/min between 0 and 600 pounds per square inch. This cycling occurred for 5 trials. As before, load vs. photon emission data were recorded by the oscilloscope 30 and stress vs. strain data was taken directly from the unit 22.

Further, cycling was carried out of the range 0-1000 psi (substantially past linear/elastic region). A 5 mm cube sample 24 of irradiated LiF was inserted into the unit 22 and the anvils 26a, 26b were started together at 0.002 inches/min between 0 and 1000 pounds per square inch. This cycling occurred for 5 trials. As above, load vs. photon emission data were recorded by the oscilloscope 30 and stress vs. strain data was taken directly from the unit 22.

In addition, cycling was carried out over the range of 0-2000 psi (high stress). A 5 mm cube sample 24 of irradiated LiF was inserted into the unit 22 and the anvils 26a, 26b were started together at 0.002 inches/min between 0 and 2000 pounds per square inch. This cycling occurred for 5 trials. As before, load vs. photon emission data were recorded by the oscilloscope 30 and stress vs. strain data was taken directly from the unit 22.

Further, cycling was carried out over the range of 0-3000 psi (severe stress). A 5 mm cube sample 24 of irradiated LiF was inserted into the unit 22 and the anvils 26a, 26b were started together at 0.002 inches/min between 0 and 3000 pounds per square inch. This cycling occurred for 5 trials. Load vs. photon emission data were recorded by the oscilloscope 30 and stress vs. strain data was taken directly from the unit 22.

Finally, cycling was carried out over a range of 0-4000 psi (extreme range). A 5 mm cube sample 24 of irradiated LiF was inserted into the unit 22 and the anvils 26a, 26b were started together at 0.002 inches/min between 0 and 4000 pounds per square inch. This cycling occurred for 5 trials. As in the other cycling tests, load vs. photon emission data were recorded by the oscilloscope 30 and stress vs. strain data was taken directly from the unit 22.

As a result of the testing described above, it was concluded that, regarding compression, the linear/elastic region ended at the critical yield point of Lithium Fluoride (LiF) crystal sample 24, viz., at 300 psi. Upon plastic deformation of the sample 24, deformation luminescence sporadically appears at low levels. However, no substantial emission of photons occurs until the specimen reaches its yield point.

In the compression control experiment of the 5 mm irradiated LiF crystal, in general, no photons were emitted below the 300 psi critical point. Just prior to the critical point, however, light began to emerge. As the load increased in a linear fashion (constant crosshead speed) beyond the yield point, the photon emissions was found to increase logistically, in accordance with the formula:

$$\frac{dI}{dt} = kI(I_{max} - I)$$

where I is photon emission, k is a specific constant, t is time. Thus, the rate of photon emission intensity over time increased logistically. This differential equation can be integrated into a more usable form as follows:

$$I = \frac{I_{max}}{1 + be^{-ct}}$$

where $I_{max}$, b and c are constants. When photon emission intensity reaches the level $I_{max}$, the intensity decays linearly in the form:

$$I = -mt + c$$

where m is the slope of decay and c is a constant.

The stress/strain data that was derived strongly indicates hysteresis in the crystal. It was found that as stress increases beyond the elastic region, the rate of the increase in percent strain drops dramatically. The stress/strain relationship within the linear/elastic region can be quantified in the form:

$$\epsilon = m\delta + b \text{(slope intercept form)}$$

where $\epsilon$ is percent strain, $\delta$ is stress in psi, m is the rate at which x increases, and b is zero because there is no strain when stress is absent. When stress exceeds the 300 psi critical point, hysteresis occurs and strain no longer is linear with stress.

As a function of stress, photon emission grew logistically, modified by linear decay. However, as a function of strain, the photon emission grew in a pure logistic curve.

In cycling tests, for the testing of hysteresis, a load range of 300 psi and a subsequent load of 600 psi were chosen. For the cycling between 0-300 psi, light first emerged in low quantities, around 1.5 million photons per second. When the load finally hit 300 psi, photon emissions increased to 250 million photons per second. DL dropped more than 60% after the first cycle and dropped 20% in each subsequent cycle. The corresponding stress vs. strain data showed that the first cycling range was well within the linear/elastic region.

In testing that was also carried out at various load speeds, it was found that the speed of crosshead also affected photon emission. By taking the averages of multiple data points and crosshead speeds, the speed of the anvils 26a, 26b was calculated to be logarithmically proportional to the intensity of photon emission. Thus, light increases by an order of 10, while speed increases linearly.

It is noted that non-irradiated LiF did not exhibit deformation luminescence. Light was, however, emitted as loads reached extreme ranges. Spikes of light were detected at fractures.

In testing wherein there was artificial surface fracture, artificial cracks on the irradiated crystal greatly increased the production of photons. At similar loads, light production was boosted 700-1000%.

In four trials that involved a crystal fracture, the total photon counts were summed. After correcting for size differences and absorption, the average accumulative photon count equaled 57 trillion photons for a 800 kR dosed 1 cm LiF crystal. The standard deviation was 11%.

Considering the testing discussed above in more detail, and turning first to the compression testing, for the compression of 5 mm cubic crystal, the intensity of deformation luminescence closely correlates with the stress and strain relation. At low levels of stress and strain, trace levels of light were observed. When the yield point of deformation (which was observed to be at stress of 300 psi) as approached, light intensity starts to enter two periods of logistical growth. As stress and strain move up into the non-elastic range where significant deformation is created and hysteresis begins to take effect, light intensity drastically increases until the intensity limits off to the maximum constant. This occurrence shows that the number of F centers available at each stress/strain level is limited. Therefore, the intrinsic number of F centers created by ionizing radiation limits photon emissions. This trend shows that there are different levels of F centers that respond to increasingly high levels of stress. Surprisingly, photon emissions were detected within the linear region. This suggests that internal fatigue occurs even when the material is stressed weakly.

With respect to the correlation of stress and strain with DL, as a function of stress, DL increases logistically with a decay function. This shows that DL increases exponentially with stress. However, as stress increases, DL begins to fade and decay. This suggests that the total amount of DL emissions is a better indicator of the total health of the material than the emissions at a specific point. F-centers appear to exist in tiers where specific stress thresholds are able to unlock a limited number of F-centers.

As a function of strain, the increase in DL follows a modified growth curve. This indicates that the DL increases towards a limit, as compared to strain. This differs from stress because strain slows down at similar rates as DL. This suggests that rates of strain and DL emissions are very similar, and more similar than the rates for stress DL.

Regarding cycling, when stress, under the 300 psi yield point, was cyclically applied to a 5 mm irradiated sample, the crystal was able to return to its original dimensions every time. Hooke's Law of Elasticity states that if a force (F) is applied to an elastic spring or prismatic rod (with length L and cross section A), its extension is linearly proportional to its tensile stress ($\sigma$) and modulus of elasticity (E), as represented by the formula:

$$\Delta L = 1/E \times F \times L/A = 1/E \times L \times \sigma$$

This law holds until force exceeds the elastic limit, which causes the material to yield and suffer plastic deformation (see *Hooke's Law*. Wikipedia. 17 Dec. 2004). Within the elastic region of the material, low levels of photon emission were observed. This effect indicates that some F centers of the crystal have already been dislocated and released electrons into the conduction band prior to the yield point. This suggests that the material is suffering damage well within the elastic region.

When stress was increased beyond the elastic limit, photon emission increased 600-fold. When the stress was released, the crystal no longer could return to its original dimension; the material had undergone hysteresis. Therefore, deformation luminescence is an indicator of material going through deformation and fatigue.

As discussed above, when cycling at the same stress, DL dropped significantly, more than 50%, on the second cycle, and subsequent cycles decayed about 20% each time. This indicates there is a gradual decrease in viable F-centers after stress.

More generally, it will be appreciated from the foregoing that the cumulative total of photons (and/or other particles) emitted up to fracture is essentially constant, even under drastically different stress regimens. This constant value can be determined or calculated for each type of material by, e.g., experimental trials. When the count of photons (and/or other particles) approaches the predetermined statistical range around the calculated constant, the material will be in imminent danger of fracture and failure.

With respect to cracks within the lattice of a material, both irradiated and non-irradiated crystals emit light when fractures occur, although the mechanism may be different. Nonetheless, deformation luminescence is still a reliable indicator of material fracture that may not be immediately obvious. Substantial amounts of photons are emitted, even during the perceived "safe" elastic range, when cracks are present. This is due to the fact that stress is focused and magnified around the edges of cracks within the material. In this regard, the internal stress of the material with cracks could be dangerously high even the applied external stress is not. Because of this, deformation luminescence is believed to be a very useful tool in detecting unseen or invisible cracks within materials. Moreover, as indicated above, deformation luminescence provides invaluable data in connection with material failure.

Generally speaking, the present invention can be used to detect the presence of "invisible" cracks within materials because the presence of such cracks, which may lead to failure, cause an increase in photonic emissions by several-fold over normal, undamaged materials. As indicated above, internal cracks are thought to focus and concentrate the stress in localized areas around the edges of the cracks and, therefore, increase the emissions of photons (and/or other particles). Also, when cracks or small fractures are created, a spike of emissions is generated. It is noted that even where there is no existing crack, a sudden spike of light will indicate that a fracture or crack has just occurred. This happens even without radiation of the material and is caused by triboluminescence, which was discussed above.

Regarding the effect of load speed, deformation luminescence was observed to increase as the speed of stress application increased. Further testing explored the relationship between luminescence and the speed of stress applied. In this testing, a load of 300 psi was applied at three different speeds of 0.002 inch/sec, 0.016 inch/sec and 0.032 inch/sec. It was found that intensity increases logarithmically with speed. The increase would be expected in that a rapidly applied stress would appear to be more likely to create material damage than a slowly applied stress. This indicates that deformation luminescence provides useful information with respect to stress and strain analysis above and beyond that provided by Hooke's Law which provides no information as to how the speed of stress relates to internal fatigue.

Regarding fracture, when a fracture occurred within the crystal, a sharp spike of light was emitted. The sudden break of the material is clearly shown by the jump in photon emission. Such signals show that DL not only is a good indicator of hysteresis, but it is even an indicator of material failure.

With respect to the non-irradiated samples, in the control experiments of non-irradiated 1 cm crystal, photon emission was not observed during compression of the sample. However, as indicated above, light was observed when the crystal fractured at 1200 psi. This indicates that ionizing radiation may be required to create F centers within the crystalline lattice structure. This also indicates that a triboluminescent phenomenon may have occurred at the fracture, which has different mechanism than deformation luminescence. In this case, triboluminescence was caused by opposite electrical charges separated under mechanical pressure creating sparks across the crack.

Material failure can be predicted from the accumulative photons emitted. The integral of the DL vs. time curve, i.e., the cumulative total of photons emitted until failure, appears to be constant even when stress regimens were radically different. During the trials discussed above, the standard deviation of the integral was 11% around 57 trillion photons. Thus, photon counts can be used to predict material failure. In this regard, the cumulative photon count can be utilized as a "clock" for measuring the aging and deterioration of a material. The useful life of a material remaining can, therefore, be predicted by the number of photons "left" within the system. When the photon count reaches the limit (which is empirically derived), the material's clock has run out; the material fails and breaks. Although the use of DL is not effective for determining how much damage is caused by each specific impact, the cumulative total is an effective measure of how much total damage is sustained.

It will be appreciated from the foregoing that DL is a novel, and advantageous, method of indicating material hysteresis and is a potential predictor of material failure. Moreover, increasing stress/strain served to logistically increase photon emissions, rather than exponentially. It is believed that DL detection provides valuable data that detection of other known characteristics cannot provide. Further, the ease with which DL detection can be applied to, or incorporated into, current structures may also represent an improvement over current stress detection systems. In the latter regard, a low-maintenance photomultiplier tube is used, as opposed to the lasers that are employed with current systems, and that require complex stabilization and control mechanisms. Also, DL detection provides real-time data, indicating damage at the beginning of hysteresis. Current systems must analyze the full stress/strain curve, and thus only provide fatigue information when the material is well within hysteresis.

It is noted that DL may be linked with other physical properties, such as acoustical, thermal, and electrical characteristic of materials under stress. However, other markers will be needed because not all materials illuminate as irradiated alkali halides. DL can also be used in measuring subtle changes in photon emission patterns prior to material failure, at nanoscale level, using ultrahigh resolution equipment. Further, plastics, ceramics, and other non-conductive, semi-transparent materials exhibit DL properties and the invention is applicable to such materials as well. It is noted that some of these materials may require the use of radiation, or other means, to dislocate or dislodge the electrons to higher energy levels in order for the basic approach disclosed here to work.

Although the invention has been described above in relation to preferred embodiments thereof, it will be understood by those skilled in the art that variations and modifications can be effected in these preferred embodiments without departing from the scope and spirit of the invention.

What is claimed:

1. A method for predicting failure of a material, said method comprising the steps of:
    detecting photonic emissions from a material under test and counting the number of photons emitted by the material over time; and
    comparing the number of photons counted with a predetermined constant value based on the cumulative total of photons at failure for a comparable material so as to predict incipient failure of the material under test.

2. A method as claimed in claim 1 wherein the detecting step comprises measuring the intensity of deformation luminescence produced by the material.

3. A method according to claim 2 wherein a photomultiplier tube is used in the detecting step.

4. A method for detecting fatigue in a material, said method comprising the steps of:
    detecting photonic emissions from the material, the detecting step comprising the step of counting the number of photons emitted; and
    using the detected photonic emissions to determine fatigue in the material and in the determination of fatigue, a determination is made as to when the number of photons counted in the counting step approaches a predetermined constant value calculated based on a cumulative total for photon emissions up to fracture.

* * * * *